United States Patent [19]

Wong et al.

[11] Patent Number: 5,576,426
[45] Date of Patent: Nov. 19, 1996

[54] ALDOLASE CATALYZED STEREOSELECTIVE SYNTHESIS OF ARABINOHEXULOSE, XYLOHEPTULOSE, THREOHEXULOSE AND XYLOHEXULOSE

[75] Inventors: Chi-Huey Wong, Rancho Santa Fe, Calif.; John R. Durrwachter, Corpus Christi, Tex.; Richard L. Pederson, Bend, Oreg.

[73] Assignee: G. D. Searle & Co., Chicago, Ill.

[21] Appl. No.: 303,289

[22] Filed: Sep. 8, 1994

Related U.S. Application Data

[60] Continuation of Ser. No. 857,016, Mar. 24, 1992, abandoned, which is a division of Ser. No. 238,756, Aug. 30, 1988, Pat. No. 5,143,831.

[51] Int. Cl.$^6$ .................... C07H 5/04; C07H 5/06
[52] U.S. Cl. ............................................. 536/18.7
[58] Field of Search ........................... 536/18.7

[56] References Cited

U.S. PATENT DOCUMENTS

| | | | |
|---|---|---|---|
| 2,875,194 | 2/1959 | Baker et al. ......................... | 536/18.7 |
| 4,440,854 | 4/1984 | Whitesides et al. ................... | 435/94 |

OTHER PUBLICATIONS

Chemical Abstracts, vol. 93, No. 5, issued 4 Aug. 1980, Stoltefuss et al, "α'–Glucosidase Inhibitors", see p. 766, column 2, abstract No. 44655s, Ger. Offen. 2,830,424, 31 Jan. 1980.

Thomas Ziegler et al Enzyme–Catalyzed Synthesis of etc. Angew. Chem. Int. Ed. Engl 27 No. 5 716–717 Jan. 1988.

Drueckhammer et al. Reversible and in Situ Formation of Organic etc. J. Org. Chem. 54 70–77 Jan. 1989.

Durrwachter et al. Fructose 1,6–Diphosphate Aldolase Catalyzed etc. J. Org. Chem. 53 4175–4181 Jan. 1988.

Wong et al. Synthesis of Sugars by Aldolase–Catalyzed etc. J. Org. Chem. 48 3199–3205 Jan. 1983.

Dr. H. Paulsen Carbohydrates Containing Nitrogen or Sulfur in etc. Angew. Chem. Intl. Ed. Eng. 5(5) 495–511 Jan. 1966.

Durrwachter et at. Enzymatic Aldol Reaction/Isomerization As A etc. Tetrahedron Letters V 27 N 11 1261–1264 Mar. 1986.

Wong et al. Chemical and Enzymatic Syntheses of etc. J. Org. Chem. 48(20) 3493–3497 Jan. 1983.

Durrwachter et al. Enzymatic Aldol Condensation/Isomerization as etc. J. Amer. Chem Soc. 108(24) 7812–7818 Jan. 1986.

Primary Examiner—John Kight
Assistant Examiner—Everett White
Attorney, Agent, or Firm—Cynthia S. Kovacevic; Roger A. Williams

[57] ABSTRACT

The present invention relates to aldolase catalyzed stereoselective synthesis of sugars and compositions of matter comprising arabinohexulose, xyloheptulose, threohexulose, and xylohexulose.

1 Claim, No Drawings

ALDOLASE CATALYZED STEREOSELECTIVE SYNTHESIS OF ARABINOHEXULOSE, XYLOHEPTULOSE, THREOHEXULOSE AND XYLOHEXULOSE

This is a File-Wrapper continuation, of application Ser. No. 07/857,016, filed Mar. 24, 1992, now abandoned, which is a divisional application of U.S. Ser. No. 07/238,756, filed Aug. 30, 1988, issued as U.S. Pat. No. 5,143,831 on Sep. 1, 1992.

The present invention relates to new aldehydes and new processes for producing substantially optically pure sugars using racemic substrates, and to new C-alkyl and N-containing sugars produced using such processes.

Several methods have been used to produce substantially optically pure sugars in the past. For example, enzymatic transformations have been used as alternative methods in enantioselective synthesis. Many useful reactions, particularly those based on the use of hydrolases and oxidoreductases have been demonstrated. Enzyme-catalyzed aldol condensations also have been shown synthetically useful. E.g., Wong, C-H., Whitesides, G. M. *J. Org. Chem.* 48 (1983) 3199; Wong, C-H., Mazenod, F. P., Whitesides, G. M. Ibid. 3493; Durrwachter, J. R., Drueckhammer, D. G., Nozaki, K., Sweers, H. M., Wong, C-H. *J. Am. Chem. Soc.* 108 (1986) 7812; Wong, C-H. "Enzymes as Catalysts in Organic Synthesis," Schneider, M. P., Ed. Reidel: Dordrecht (1986) 199; Bednarski, M. D., Waldmann, H. J., Whitesides, G. M. *Tetrahedron Lett.* 27 (1986) 5807; Reimer, L. M., Conley, D. L. Pompliano, D. L., Frost, J. W. *J. Am. Chem. Soc.* 108 (1986) 8010; Mocali, A., Aldinucci, D., Paoletti, F. *Carbohydr. Res.* 143 (1985) 288; Kapusinski, M., Franke, F. P., Flanigan, I., MacLeod, J. K., Williams, J. F. Ibid. 140 (1985) 69; Auge, C., Gautheron, C. *J. Chem. Soc., Chem. Commun.* (1987) 859; David, S., Auge, C. *Pure Appl. Chem.* 59 (1987) 1501. Enzymatic synthesis normally are carried out in aqueous solution under mild conditions and with no protection of the functional groups of the substrate.

More than fifteen aldolases have been isolated, each of which catalyzes a distinct type of aldol reaction. Wong, C-H. "Enzymes as Catalysts in Organic Synthesis," Schneider, M. P., Ed. Reidel: Dordrecht (1986) 199. The enzyme fructose 1,6-diphosphate (FDP) Aldolase has been used for synthesis of a number of common and uncommon sugars including deoxyhexoses, fluoro sugars, $^{13}$C-labeled sugars, and many high-carbon sugars. The enzyme is specific for dihydroxyacetone phosphate (DHAP) as the aldol donor, but will accept a variety of aldehydes as acceptors. As an alternative to DHAP as the aldol donor, dihydroxyacetone (DHA) along with a catalystic amount of inorganic arsenate may be used. Durrwachter, J. R., Drueckhammer, D. G., Nozaki, K., Sweers, H. M., Wong, C-H. *J. Am. Chem. Soc.* 108 (1986) 7812. The stereochemistry of the newly formed C—C bond is the same in all aldol reactions studied so far. The chiral environment in the aldehyde acceptors does not affect the stereochemistry of the C—C bond formation.

The major obstacle encountered in enzymatic aldol condensation is that the preparation of aldehyde acceptors is difficult, particularly if an enantiomerically pure aldehyde is required. Another potential problem is that many interesting α-substituted chiral aldehydes are not stable in aqueous solution, prohibiting the preparation of many interesting uncommon sugars.

SUMMARY OF THE INVENTION

The present invention provides thermodynamically and kinetically controlled syntheses of diestereomerically pure sugars using racemic aldehydes as substrates. Because of the reversible nature of the aldol reaction, and the favorable equilibrium position in the condensation direction, a thermodynamically more stable product (i.e., the product having 1–2 kcal/mol less energy than the other diastereomer), or a kinetically favored product, can be selectively obtained.

DETAILED DESCRIPTION OF THE INVENTION

In the following experiments, FDP aldolase (EC 4.1.2.13) from rabbit muscle and other enzymes and biochemicals were purchased from Sigma. FDP aldolase alternatively can be isolated from bacterial sources (e.g., from *E. coli*) or from yeast. Baldwin, S. A., Perham, R. N., Stribling, D. *Biochem. J.* 169 (1978) 633 (*E. coli*), incorporated herein by reference; Richards, O. C., Rutter, W. J. *J. Biol. Chem.* 236 (1961) 3177 (yeast), incorporated herein by reference. The solvents and chemicals used were of reagent grade. Dihydroxyacetone phosphate (DHAP) was generated in situ from FDP-Na$_3$ in the presence of FDP aldolase and triose phosphate isomerase (TPI) according to the procedure described in Durrwachter, J. R., Drueckhammer, D. G., Nozaki, K., Sweers, H. M., Wong, C-H. *J. Am. Chem. Soc.* 108 (1986) 7812, incorporated herein by reference. As an alternate procedure, dihydroxyacetone (DHA) and a catalytic amount of inorganic arsenate may be used in place of DHAP. Ibid. Optical rotations were measured on a Perkin-Elmer 240 Polarimeter. Proton, $^{13}$C, and fluorine NMR spectra were obtained on Varian XL-200 or XL-400 spectrometers operating at 200 and 400 MHz, respectively. All chemical shifts were reported in ppm with tetramethylsilane as an internal standard unless otherwise indicated. UV spectra were taken with a Beckman DU-70 instrument. HPLC analyses were done on a Gilson chromatography system including a Model 302 pump, Model 131 refractive index detector, and a Rheodyne injector. Gas chromatography (GC) analyses were performed on a Hewlett-Packard 5890 instrument. Nicolet R3n/v X-ray diffractometer and ShelXTL (version 5) software were used in the single/crystal x-ray structure determination.

The general scheme of the reaction occurring in the following examples in diagrammed below:

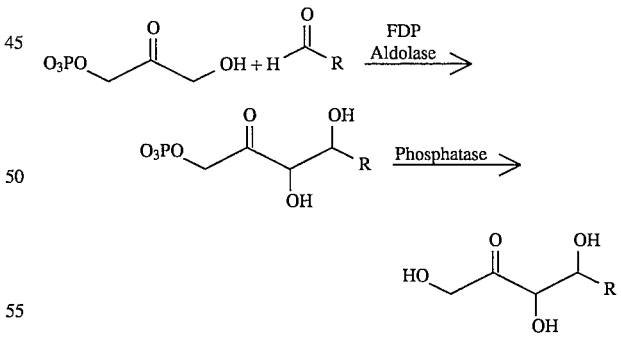

It was discovered that, when sugars are formed by aldol condensation using aldehydes having a hydroxyl group at the B-position, the D-enantiomer is thermodynamically more stable and will be the sole product formed. For aldehydes that are not hydroxylated at the B-position, an optically pure product can be obtained by monitoring and stopping the reaction once a second diastereomer is detected by the monitoring.

Some of the intermediates and sugars formed in the following examples were unstable because of their N-containing functional groups. Often a product having desired characteristics can be obtained by manipulating the structure of such an N-containing functional group in the aldehyde acceptor. For example, the following compound (6-deoxy-6-X-D-arabino-hexulose) is valuable as a substrate for producing deoxymannojirimycin, as described in copending application Ser. No. 07/247,276 filed Sep. 21, 1988, now abandoned.

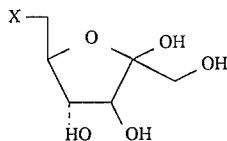

The structure of X is unimportant except that X must contain nitrogen. Thus, the relatively stable compound 6-azido-6-deoxy-D-arabino-hexulose (Example 3) can be used rather than the unstable compound 6-deoxy-6-(trifluoroacetamide)-D-arabino-hexulose (Example 2).

N-Containing Sugars

Sugars containing nitrogen in the ring have been prepared by several workers. Paulsen, H., Todk, K. *Adv. Carbohydr. Chem.* 23 (1968) 115; Hanessian, S. *Chem. Ind.* (1966) 2126. Kinast, G., Schedel, M. *Angew, Chem. Int. Ed. Engl.* 20 (1981) 805. Haman, H., Ikota, N., Ganem, B. *J. Org. Chem.* 52 (1987) 5494; Inouye, S., Tsuruoka, T., Ito, T., Niida, T. *Tetrahedron* 23 (1876) 2125. These sugars are interesting because of their natural rarity, their potent biological effects (e.g., as antibiotics or glycosidase inhibitors), and their synthetic challenge. These sugars, as well as aminoaldehydes, are not stable and must be prepared in some derivative form.

Example 1-Preparation of 5,6-dideoxy-6-(trifluoroacetamido)-D-threo-hexulose

To 500 ml of dimethylformamide (DMF) containing NaN₃ (26.0 g, 400 mmol) was added 3-chloropropionaldehyde diethyl acetal (33.3 g, 200 mmol). The solution was warmed to 60° C., and the reaction was monitored by GC (50° C., 1 min to 250° C. at 15° C./min, DB5–15 m). (Retention time ($t_R$) of starting material 5.1 min, product 6.5 min). The reaction mixture was diluted with 1 L of ice water and extracted with ether (3×500 mL). The combined ether extracts were washed with water (2×500 mL) and then dried over MgSO₄. Removal of solvent afforded a crude product, which was dissolved in 500 mL of ethanol containing Pd/C (10%, 2.03 g, 2 mmol). The suspension was degassed, saturated with H₂, and stirred under an H₂ balloon for four days at which time GC analysis of the product amine ($t_R$ 5.4 min) indicated a complete reaction. The solution was degassed and filtered through Celite 545, and the solvent was removed under reduced pressure. The residue was diluted with 25 mL of 12N KOH and extracted with ether (2×50 mL). The ether layer was filtered through glass wool/Na₂CO₃ and dried over Na₂CO₃. The solvent was removed under water aspirator vacuum, and the residue was distilled to yield 3-aminopropanal diethylacetal (18.6 g, 126 mmol, 63%): bp₁₇ 80°–81.5° C. bp₂₀ 68°–70° C. agreed with b.p. in Becke, F. German Patent 845,348, 1952, *Chem. Abstr.* 47 (1952) 542); ¹H—NMR (200 MHz CDCl₃) δ 1.21 (t, 6 H, CH₃), 1.58 (s, 2 H, NH₂), 1.78 (q, 2 H CH₂), 2.81 (t, 2 H, NCH₂), 3.53 and 3.66 (m, 4 H, OCH₂), 4.62 (t, 1 H, CH). Anal. Calcd for C₇H₁₇NO₂: C, 57.1; H, 11.6. Found: C, 57.1; H, 11.5.

To 15 mL of ethyl trifluoroacetate (127 mmol) was added the above product (4.8 g, 33 mmol). The reaction was over immediately as shown by GC analysis ($t_R$ 7.9 min, same conditions as above). The solvent was removed under reduced pressure to yield 3-(trifluoroacetamido)propanaldiethyl acetal, an aldehyde precursor having the following structure:

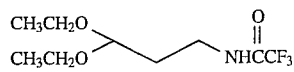

(5.2 g, 21 mmol, 65% yield): ¹H—NMR (200 MHz CDCl₃) δ 1.23 (t, J=7.0 Hz, 6 H, CH₃), 1.90 (m, 2 H, CH₂), 3.50 (m, 2 H, CH₂N), 3.52, 3.73 (dq, J=9.2 Hz, J=7.0 Hz, 4 H, CH₂O), 4.63 (t, J=4.6 Hz, 1 H, CH). ¹³C—NMR (50 MHz, CDCl₃) δ 14.72 (CH₃), 31.69 (CH₂), 35.38 (CH₂N), 62.25 (CH₂O), 102.13 (CH), 115.73 (q, J=287 Hz, CF₃), 156.69 (q, J=36.5 Hz, C—O); ¹⁹F NMR (376 MHz, CDCl₃) δ —13.99 (s, CF₃).

Into 5 mL of water containing 50 µL of CH₃SO₂OH was introduced the 3-(trifluoroacetamido)propanol-diethyl acetal (1.08 g, 4.5 mmol). The solution was stirred at room temperature and monitored by GC under the same conditions as above ($t_R$ of 3-(trifluoroacetamido)-propanal-diethyl acetal 7.9 min). After completion of hydrolysis, FDP-Na₃ (825.6 mg, 1.5 mmol) in 10 mL H₂O was added, and the pH was adjusted to 6.5 with NaOH. After degassing with argon, aldolase (300 units) and triose phosphate isomerase (TPI, 500 units) were added. (The two enzymes generate 2 equivalents of DHAP in situ from FDP-Na₃.) After 24 h, the reaction was stopped by the addition of a solution of BaCl₂·2H₂O(1.485 g, 6.1 mmol). The pH was adjusted to 7.8 with NaOH and diluted with 20 mL of acetone. The precipitate was isolated by centrifugation and washed with acetone (2×25 mL). The white solid was suspended in 25 mL of water, and HCl was added to a pH of 1. A solution of Na₂SO₄ (850 mg, 6 mmol) was added and the pH was adjusted to 6.5 with NaOH. The suspension was filtered through Celite 545 to remove barium sulfate. The pH of the filtrate was adjusted to 4.9 with acetic acid, and acid phosphatase (100 units) was added. After 12 h, the reaction was complete and TLC (silica gel, ethyl acetate-methanol-H₂O, 12:6:2, $R_f$ of 5,6-dideoxy-6-(trifluoro-acetamido)-D-threo-hexulose 0.76, fructose 0.35) indicated only a trace of fructose (undetectable by NMR). The solution was neutralized and then freeze-dried. The residue was triturated with ethanol to yield, after removal of solvent, a relatively clean sample of 5,6-dideoxy-6-(trifluoroacetamido)-D-threohexulose, a compound having the following structure:

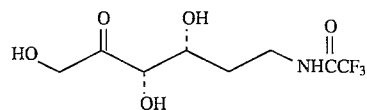

Purification by chromatography (silica gel, water saturated ethyl acetate) yielded said compound as a reddish oil (320 mg, 1.23 mmol, 41% yield): [α]²⁸_D, 4.1 (c 3.2, ethanol); ¹H—NMR (200 MHz, D₂O) δ 1.5–1.8 (m, 2 H, CH₂), 3.20–4.55, a complex series of peaks of 6 H, 3.31 (t), 3.40–3.65 (low multiplets), 3.71 (dt), 3.89 (dt), 4.14 (2 d), 4.25 (d), 4.37 (2 d), 4.50 (d), 5.04 (t); ¹³C—NMR (50 MHz D₂O) δ 33.83 (C5), 39.21 (C6), 68.71, 72.04, 80.22 (CHOD), 118.50 (q, J=286 Hz, CF₃), 161.50 (q, J=37.2 Hz); ¹⁹F NMR (376 MHz, D₂O) δ −10.94, −10.91, −10.66 (s).

Anal. Calcd for $C_8H_{12}O_5NF_3$: C, 37.21; H, 4.65; N, 5.43. Found C, 37.11; H, 4.58; N, 5.44. The pH of the $^{13}C$ sample was adjusted to 7.5 with $K_2CO_3$. After 24 h, very little hydrolysis of the trifluoroacetate was observed. Upon adjusting the pH to ≅10, the hydrolysis proceeded much faster. In either case, new peaks appear that would imply the piperidinose sugar. The sample, however, degraded, resulting in the rapid coloration and the decreased signal to noise ratio.

Example 2-Preparation of 6deoxy-6-(trifluoroacetamido)-D-arabino-hexulose

Into a three-neck flask fitted with a stirring bar and pH probe was placed glycidaldehyde diethyl acetal (17.59 g, 102 mmol, 85% pure), 50% ethanol in water (250 mL), and $NaN_3$ (13.35 g, 205 mmol). The pH was adjusted to and maintained at 7.5 with aqueous $H_2SO_4$. The solution was warmed to 50° C. for 12 h. GC analysis (40° C., 5 min to 250° C. at 15° C./min, DB-5, $t_R$ of epoxide 5.65 min, product 10.0 min) indicated complete reaction. The ethanol was removed under reduced pressure, and the aqueous solution was saturated with $Na_2SO_4$. This was extracted with ethyl acetate (3×80 ml) and the combined organics dried over $Na_2SO_4$. Removal of solvent by evaporation followed by distillation of residue yielded D,L-3-azido-2-hydroxypropanol diethyl acetal, an aldehyde precursor having the following structure:

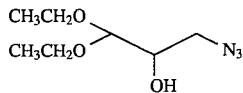

(17.8 g, 86.7 mmol, 85% yield) $bp_{2.8}$ 96°–97° C.; $^1H$—NMR (200 MHz, $CDCl_3$) δ 1.23 and 1.26 (t, J=7.1 Hz, 6 H, $CH_3$), 2.47 (d, J=6 Hz, OH), 3.35 (dd, J=6 Hz, J=12.8 Hz, 1 H, $CH_2N_3$), 3.51 (dd, J=3.6 Hz, J=12.8 Hz, 1 H, $CH_2N_3$), 3.60 (m, 1 H, CHOH), 3.77 (m, 4 H, $OCH_2$), 4.47 (d, J=6.2 Hz, 1 H, CH); $^{13}C$—NMR (50 MHz, $CDCL_3$) δ 15.69, 15.73 ($CH_3$), 52.8 ($CH_2N_3$), 64.1, 64.5 ($CH_2O$), 71.9 (CHOH), 103.2 (CHOEt).

To a suspension of Pd/C (10%, 0.5 g, 0.5 mmol) in 150 mL of ethanol was added D,L-3-azido-2-hydroxypropanol diethyl acetal (8.04 g, 39 mmol). The mixture was degassed and hydrogenated under a hydrogen balloon for 24 h. The reaction was monitored by GC (50° C., 1 min to 250° C. at 15° C./min, DB-5; $t_R$ of azide 7.4 min, amine 6.4 min). The ethanol was removed under reduced pressure, and the residue was distilled to yield (D,L)-3-amino-2-hydroxy-propanal diethyl acetal (5.3 g, 33 mmol, 83%, $bp_{0.03}$ 59° C.; solidified upon cooling, mp 45° C.): $^1H$—NMR (200 MHz, DMSO) δ 1.08, 1.10 (t, J=7.0 Hz, 6 H, $CH_3$), 2.41 (dd, J=7.4 Hz, J=13.0 Hz, 1 H, CHN), 2.62 (dd, J=3.8 Hz,J=13.0 Hz, 1 H, CHN), 3.27 (ddd, J=3.8 Hz, J=7.4 Hz, J=6.0 Hz, 1 H, CHO), 3.35–3.69 (m, 4 H, $CH_2O$), 4.21 (d, J=6.0 Hz, 1 H, CH); $^{13}C$—NMR (50 MHz, DMSO) δ 15.32, 15.39 ($CH_3$), 43.63 ($CH_2NH_2$), 61.72, 62.48 ($CH_2O$), 72.51 (CHO), 103.83 (CH).

To 30 mL of ethyl trifluoroacetate (250 mmol) was added (D,L)-3-amino-2-hydroxypropanal diethyl acetal (4.5 g, 26 mmol). The reaction was over immediately as determined by GC (same condition as above, $t_R$ of D,L-2-hydroxy-3-(trifluoroacetamido) propanal diethyl acetal 8.1 min). The solvent was removed under reduced pressure, and the residue was distilled to yield D,L-2-hydroxy-3-(trifluoroacetamido) propanal diethyl acetal, an aldehyde precursor having the following structure:

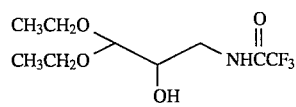

(5.1 g, 19.7 mmol, 76% $bp_{0.06}$ 62° C.). The sample solidified upon cooling, mp 42° C.: $^1H$—NMR (200 MHz, DMSO) δ 1.10, 1.11 (t, J=7.0, 6 H, $CH_3$), 3.14 (ddd, J=13.3 Hz, J=8.6 Hz, J=6.0 Hz, 1 H, CHN), 3.33 (ddd, J=13.3 Hz, J=3.5 Hz, J=6.0 Hz, 1 H, CHN), 3.40–3.72 (m, 5 H, $CH_2O$, CHO), 4.25 (d, J=4.5 Hz, 1 H, CH), 5.05 (d, J=5.6 Hz, 1 H, OH), 9.22 (t, J=6.0 Hz, 1 H, NH); $^{13}C$—NMR (50 MHz, DMSO) 15.22, 15.31 ($CH_3$), 41.59 ($CH_2N$), 62.12, 63.02 ($CH_2O$), 68.87 (CHO), 103.67 (CH), 116.03(q, J=228 Hz, $CF_3$), 156.4 (q, J=36 Hz, C—O). Anal. Calcd for $C_9H_{16}NO_4F_3$: C, 4.17; H, 6.2; N, 5.4. Found C, 41.72; H, 6.23; N, 5.70.

Into a solution of 15 mL of $H_2O$ and 200 μL of HCl was dissolved the D,L-2-hydroxy-3-(trifluoroacetamido)propanal diethyl acetal (1.036 g, 4 mmol). The solution was warmed to 38° C. After complete hydrolysis of the acetal (15 h, by GC), FDP-$Na_3$ (593 mg, 1.08 mmol) was added and the pH was adjusted to 6.8 with NaOH. The solution was degassed with argon, and aldolase (300 units) and TPI (500 units) were added. Twenty hours later, the reaction was complete and the mixture was treated as before to remove the phosphate moiety, resulting in a mixture in which NMR analysis detected 6-deoxy-6-(trifluoroacetamido)-D-arabino-hexulose. Further purification by chromatography on Dowex 50-$Ba^{2+}$ resulted in a complete loss of product.

Example 3-Preparation of 6-azido-6-deoxy-D-arabino-hexulose

Into 10 mL of $H_2O$ containing 150 μL of concentrated HCl was added D,L-3-azido-2-hydroxypropanal diethyl acetal (836 mg, 4 mmol), obtained as described in Example 2. The solution was warmed to 45° C. and monitored by GC (50° C., 1 min to 250° C. at 15° C./min, DB-5, $t_R$ of the D,L-3-azido-2-hydroxypropanal diethyl acetal 7.4 min). After 12 h the reaction was complete. FDP-$Na_3$ (570 mg, 1.04 mmol) was added, and the pH was adjusted to 6.5 with NaOH. Aldolase (300 units) and TPI (500 units) were added, and the solution was degassed with argon. After 24 h, the solution was treated as before to remove the phosphate moiety. The resulting solid was triturated with methanol (3×50 mL). The solvent was removed under reduced pressure, and the residue, 6-azido-6-deoxy-D-arabino-hexulose:

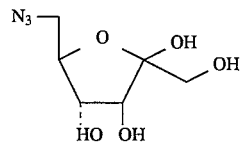

was chromatographed (Dowex 50, $Ba^{2+}$, 2×50 cm, ethanol-$H_2O$, 1:1, (v/v) to yield 290 mg, (1.4 mmol, 71%): $[\alpha]^{26}_D$ +22.2° (c 2.9, $H_2O$); $^1H$—NMR (200 MHz, $D_2O$) δ 3.18–3.56 (m), 3.66–3.86 (m), 3.89–4.06 (m), 4.11–4.29 (m), 4.36–4.45 (m); $^{13}C$—NMR (50 MHz, $D_2O$) δ 52.47 ($CH_2N_3$), 62.49, 74.92, 75.03, 78.97 (CHOH, $CH_2OH$), 101.80 ($C_2$). Anal. Calcd for $C_6H_{11}O_5N_3$: C, 35.11; H, 5.43; N, 20.5. Found: C, 35.22; H, 5.60; N, 20.66.

To further confirm the structure of 6-azido-6-deoxy-D-arabino-hexulose, the product was converted to 6-azido-6-deoxy-D-glucose. In 1 mL of water was combined the 6-azido-6-deoxy-D-arabino-hexulose (100 mg, 0.5 mmol), TAKASWEET (0.4 g, from Miles; this is the enzyme glucose isomerase), 10 μL each of 0.1M Co(NO$_3$)$_2$, 0.1M MgCl$_2$, and 1M phosphate buffer (pH 7.0), and 5 μL of 0.1M MnCl$_2$. The solution was warmed to 50° C. for 24 h. Filtration, purification through Dowex 50-Ba$^{2+}$, followed by lyophilization yielded a sample that gave a $^1$H—NMR and a $^{13}$C—NMR spectrum completely different from 6-azido-6-deoxy-D-arabino-hexulose. The $^1$H—NMR spectrum matched that of 6-deoxy-6-azido-D-glucose, indicating characteristic shifts of the aldose Cl—H at 5.22 ppm (J=2 Hz) for the α-anomer and 4.47 ppm (J=10 Hz) for the β-isomer: $^{13}$C—NMR (200 MHz, D$_2$O) δ 50.8, 50.9 (CH$_2$N$_3$), 70.1, 70.2, 70.4, 71.42, 72.5, 74.0, 74.4, 75.5 (CHOD), 92.1, 95.9, (C2). Anal. Calcd for C$_6$H$_{11}$O$_5$N$_3$: C, 35.11; H, 5.43. Found: C, 35.30; H, 5.50. Durrwachter, J. R., Drueckhammer, D. G., Nozaki, K., Sweers, H. M., Wong, C-H. *J. Am. Chem. Soc.* 108 (1986) 7812.

C-Alkyl Containing Sugars

Example 4-Preparation of
5,7-dideoxy-L-xylo-heptulose (a) Using DHAP

Freshly distilled acetylacetaldehyde dimethyl acetal (3.3 g, 25 mmol) in 200 mL of ethanol was treated with NaBH$_4$ (0.56 g, 15 mmol) in 5 mL of H$_2$O. The solution darkened and was stirred for 2 h at room temperature. The reaction was monitored by TLC (silica gel, ether-hexane, 3:1, v/v, R$_f$ starting material 0.49, product 0.39). After completion, most of the solvent was removed under water aspirator vacuum and diluted with 40 mL of H$_2$O. This solution was extracted with ethyl acetate (3×30 mL), and the combined organics were dried over Na$_2$SO$_4$. The solvent was removed under reduced pressure to yield (D,L)-3-hydroxybutanal dimethyl acetal (2.78 g, 21 mmol, 84%): $^1$H—NMR (200 MHz, CDCl$_3$) δ 1.20 (d, J=6.2 Hz, 3 H, CH$_3$), 1.75 (m, 2 H, CH$_2$), 3.08 (s, 1 H, OH), 3.35, 3.38 (s, 6 H, OCH$_3$), 3.98 (m, 1 H, CHOH), 4.58 (t, J=5.7 Hz, 1 H, CH); $^{13}$C—NMR (50 MHz, CDCl$_3$) δ 23.36 (CH$_3$), 40.98 (CH$_2$), 52.78, 53.58 (OCH$_3$), 64.45 (CHOH), 103.74 (CH).

A solution containing the above acetal (0.51 g, 3.8 mmol), 1 mL of 0.5N HCl, and 9 mL of H$_2$O was stirred for 3 h at room temperature until the hydrolysis was complete (TLC on silica gel, ether, R$_f$ acetal 0.42, aldehyde 0.23). FDP-Na$_3$ (440 mg, 0.8 mmol) was added, and the solution was adjusted to pH 7.0 with NaOH. Aldolase (125 units) and TPI (100 units) were added. After 15 h, BaCl$_2$ H$_2$O (933 mg, 3.8 mmol) was added with stirring, and the pH was adjusted to 7.3. Acetone (50 mL, 2 volumes) was added, and the solution was chilled. Centrifugation followed by washing (acetone, 2×50 mL) yielded the Ba salt of the product. The solid was suspended in 25 mL of H$_2$O with Dowex 50 (H$^+$, 4.2 g), stirred for 30 min, neutralized with NaOH, and filtered. The pH was adjusted to 4.8 with HOAc, and acid phosphatase (60 U) was added. After four days, the solution was neutralized and freeze-dried. The residue 5,7-dideoxy-1-xylo-heptulose, having the following structure:

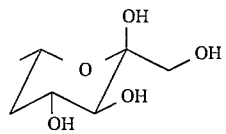

was chromatographed on a Dowex 50 (Ba$^{2+}$) column (ethanol-H$_2$O, 1:1, v/v) to yield 292 mg (1.6 mmol, 97%):

[α]$^{25}_D$-20.6 (c 1.73, H$_2$O); $^1$H—NMR (200 MHz, D$_2$O) δ 1.09 (d, J=6.2 Hz, 3 H, CH$_3$), 1.27 (m, J=12.0 Hz, J=12.8 Hz, J=11.6 Hz, 1 H, C5-H$_{ax}$), 1.94 (m, J=2.1 Hz, J=5.0 Hz, J=12.8 Hz, 1 Hm C5-H$_{eq}$), 3.33 (d, J=9.6 Hz, 1 H, C3-H), 3.39, 3.58 (Cl—H, Cl—H'), 3.83 (m, J=5.0 Hz, J=9.6 Hz, J=11.6 Hz, 1 H, C4-H 4.01 (m, J=2.1 Hz, J=6.2 Hz, Hz, 1 H, C6-H); $^{13}$C—NMR (50 MHz, D$_2$O) δ 20.29 (C7), 40.20 (C5), 64.10, 65.35, 68.28, 72.19 (Cl, 3, 4, 6) 98.03 (C2). Anal. Calcd for C$_7$H$_{14}$O$_5$: C, 47.2; H, 7.90. Found: C, 47.51; H, 7.86.

(b) Using Inorganic Arsenate

To an aqueous solution of D,L-3-hydroxy-butanal (3 mL, 3 mmol, pH 8.6, prepared in situ from acid hydrolysis (D,L)-3-hydroxybutanal dimethyl acetal, prepared as described in 4(a)), a compound having the following structure:

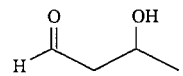

was added a solution of sodium arsenate (3 mL, 1.0M, pH 7.6). Dihydroxyacetone (0.27 g, 3 mmol) and aldolase (400 units) were added, and the solution was stirred slowly at room temperature. The reaction was monitored by HPLC with a Waters Carbohydrate column with 85% aqueous acetonitrile as the mobile phase with a flow rate of 1.2 mL/min. After 24 h, HPLC showed only a trace of 3-hydroxybutanal (t$_R$ 2.3 min) and dihydroxyacetone (t$_R$ 3.9 min) with two major new peaks (t$_R$ 4.4 and 5.9 min). Methanol was added to precipitate arsenate, and the suspension was filtered. The filtrate was applied to a Dowex 50 (Ba$^{2+}$) column (100–200 mesh, 3×75 cm) and eluted with 50% ethanol. Fractions (8 mL) were collected and analyzed by HPLC. The product with t$_P$ 4.4 min eluted first ((retention volume 240–400 mL); $^{13}$C—NMR δ 20.10 (C7), 40.18 (C5), 64.10, 65.33, 68.28, 71.01, 98.03 (C2). Anala. Calcd for C$_7$H$_{14}$O$_5$: C, 47.20; H, 7.90. Found: C, 47.11; H, 7.70)) followed by the other product (retention volume 400–800 mL). The slow-moving product was evaporated and lyophilized to give 0.19 g, which had the same NMR data as 5,7-dideoxy-1-xylo-heptulose prepared from DHAP 3-hydroxy-butanal as described above. When (S)-3-hydroxybutanal (prepared from the corresponding dimethyl acetal via acid hydrolysis as described above. The dimethyl acetal was prepared as described previously. Wong, C-H, Drueckhammer, D. G., Sweers, H. M. *J. Am. Chem. Soc.* 107 (1985) 4028, incorporated herein by reference, was used as a substrate, only 5,7-dideoxy-1-xylo-heptulose was produced, and the product with t$_R$ 4.4 was not observed.

Example 5-Preparation of
5-deoxy-6,6-dimethyl-D-threo-hexulose

CH$_3$I (18.5 mL, 297 mmol) in 50 mL of ether was added slowly, to maintain reflux, to a suspension of Mg (6.0 g, 250 mmol) in 50 mL of ether. The solution was vigorously stirred during the addition. After the magnesium was consumed, the solution was chilled with an ice bath to ≅5° C. Acetylacetaldehyde dimethyl acetal (16.5 mL, 124 mmol) in 50 mL of ether was added very slowly, over a period of 2 h. After the addition was complete, the reaction was stirred for an additional hour while warming to room temperature. The reaction was quenched with 1 mL of saturated (NH$_4$)$_2$SO$_4$(aq) and filtered. The residue was washed with ether (2×50 mL). The combined filtrates were dried over Na$_2$SO$_4$, and the solvent was removed under water aspirator vacuum (67 mmol, 54% yield). Distillation of the residue yielded 9.9 g of 3-hydroxymethylbutanal dimethyl acetal, bp$_{4.2}$ 53°–56° C. bp$_{10}$ 60°–65° C., bp$_{14}$ 72°–79° C. in agreement with Malik, O. P.; Kapil, R. S., Anand, N., *Ind. J. Chem.* 14B (1976) 449); $^1$H—NMR (200 MHz, CDCl$_3$) δ 1.24 (s, 6H, CH$_3$), 1.80 (d, J=5.9 Hz, 2 H, CH$_2$), 3.36 (s, 6 H, CH$_3$O), 3.41 (s, 1 H, OH), 4.66 (t, J=5.9 Hz, 1 H, CH), $^{13}$C—NMR (50 MHz, CDCl$_3$) δ 29.46 (CH$_3$), 43.85 (CH$_2$), 52.61 (CH$_3$O), 68.63 (COH), 102.51 (CH).

3-hydroxy-3-methylbutanal dimethyl acetal 640 mg, 4.3 mmol) was hydrolyzed in 19.9 mL of H$_2$O with CH$_3$SO$_2$OH (100 μL). After 4 h the hydrolysis was complete as determined by GC (50° C., 1 min to 250° C. at 15° C./min, DB-U; t$_R$ of acetal 4.2 min, aldehyde 2.0 min). FDP-Na$_3$ (573 mg, 1.04 mmol) was added to the solution, and the pH was adjusted to 6.5. FDP aldolase (400 units) and TPI (100 units) were added and allowed to react for 16 h. Following the same workup procedure as used in Example 1 to remove the phosphate group, the crude sugar was extracted by vigorously stirring the residue with methanol and filtering (3×50 mL). The methanol was removed under water aspirator vacuum, and the residue, 5-deoxy-6,6-dimethyl-D-threo-hexulose, having the following structure:

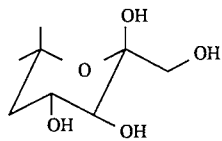

was chromatographed (silica gel, water saturated ethyl acetate), yield 0.20 g (1.04 mmol, 50%): [α]$^{25}_D$–21.8° C. (c 0.40, H$_2$O); $^1$H—NMR (200 MHz, D$_2$O) δ 1.03, 1.20 (s, 6 H, CH$_3$), 1.37 (dd, J=13 Hz, J=11.8 Hz, 1 H, axial H at C5), 1.83 (dd, J=13 Hz, J=4.7 Hz, 1 H, equatorial H at C5), 3.15, 3.42 (d, J=11.8 Hz, 2 H, CH$_2$OD), 3.27 (d, J=9.8 Hz, 1 H, C3), 3.91 (ddd, J=9.8 Hz, J=11.8 Hz, J=4.7 Hz, 1 H, C4); $^{13}$C—NMR (50 MHz, D$_2$O) δ 27.14 31.11 (CH$_3$), 43.66 (C5), 64.21, 65.82, 72.06, 75.08 (Cl, 3, 4, 6), 98.92 (C2). Anal. Calcd for C$_8$H$_{16}$O$_5$: C, 50.04; H, 8.4. Found: C, 50.2; H, 8.4.

Example 6-Preparation of 5-allyl-5-deoxy-L-xylo-hexulose

To a solution containing 4-pentenoic acid (20.73 g, 207 mmol) in ethanol (100 mL) and benzene (200 mL) was added H$_2$SO$_4$ (250 μL). The solution was refluxed and monitored by GC (50° C., 1 min to 250° C. at 10° C./min; DB-5; t$_R$ of acid 4.4 min, ester 3.8 min). After 15 h, the reaction was complete; about ½ of the solvent was removed under reduced pressure and diluted with 150 mL ether. This was extracted with H$_2$O (1×150 mL), saturated NaHCO$_3$ (2×150 mL), H$_2$O(1×150 mL), and brine (1×100 mL). The organic layer was dried over K$_2$CO$_3$, the solvent was removed under water aspirator vacuum, and the residue was distilled to yield ethyl 4-pentenoate, a compound having the following structure:

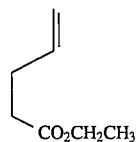

(20.79 g, 162 mmol, 78%; bp$_{760}$ 144° C.): $^1$H—NMR (200 MHc, CDCl$_3$) δ 1.25 (t, J=7.2 Hz, 3 H, CH$_3$), 2.36 (m, 4 H, CH$_2$CH$_2$), 4.14 (q, J=7.2 Hz, 2 H, OCH$_2$), 4.95–5.13 (m, 2 H, H$_2$C=), 5.81 (m, 1 H, =CH); $^{13}$C—NMR (50 MHc, CDCl$_3$) δ 14.2 (CH$_3$), 28.6, 33.5 (C—H$_2$CH$_2$), 115.3 (H$_2$C=), 136.5 (=CH), 172.8 (C=O).

To 575 mL of a chilled (–78° C.) THF/hexane (500 mL of THF/75 mL of hexane) of lithium diisopropylamide (LDA, 112.5 mmol, obtained commercially as 75 mL of 1.5M LDA in hexane) was slowly added the ethyl-4-pentenoate (12.86 g, 100 mmol) in 20 mL of THF. After the addition was complete, ethyl formate (9.1 mL, 112 mmol) was added via syringe. The reaction mixture was allowed to warm to room temperature and quenched with 15 mL of ethanol. The solution was poured into a large beaker containing ice-cold 2N H$_2$SO$_4$ (500 mL) and ether (500 mL). The contents were transferred to a 2-L separatory funnel, shaken, and separated. The ether layer was subsequently washed with 2N H$_2$SO$_4$ (1×500 mL), H$_2$O(1×500 mL), and brine (1×250 mL). The ether layer was dried over Na$_2$SO$_4$, and the solvent was removed under water aspirator vacuum to yield 40.2 g of a crude product, which was dissolved in 1 L of ethanol containing CH$_3$SO$_2$OH (0.5 mL) and warmed to 50° C. for 15 h. The reaction was monitored by GC (same condition as for the ethyl-4-pentenoate, t$_R$ of intermediate 6.6 min, of D,L-ethyl-2-(diethyoxymethyl)-4-pentenoate 11.2 min). After the reaction was complete, most of the ethanol was removed under pressure and the residue was diluted with a mixture of 250 mL of H$_2$O and 500 mL of ether. The ether layer was washed with saturated NaHCO$_3$ (2×250 mL), water (1×250 mL), and brine (1×250 mL). The ether layer was dried over Na$_2$SO$_4$, and the solvent was removed under reduced pressure. The residue was distilled to yield D,L-ethyl-2-(diethoxymethyl)-4-pentenoate, a compound having the following structure:

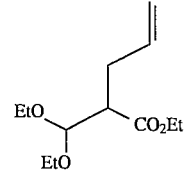

(13.98 g, 60.7 mmol, 62%): bp$_{25}$ 81°–84° C.; $^1$H—NMR (200 MHuc, CDCL$_3$)) δ 1.15, 1.22, 1.25 (3 t, J=7.0–7.4 Hz, 9 H, CH$_3$), 2.30–2.45 (m, 2 H, CH$_3$C—C), 2.78 (dt, 1 H, CHC—O), 3.45–3.80 (m, 4 H, OCH$_2$), 4.15 (q, J=7.4 Hz, 2 H, OCH$_2$), 4.65 (d, 1 H, CH), 4.9–5.15 (m, 2 H, H$_2$C—), 5.75 (m, 1 H, —CH), $^{13}$C—NMR (50 MHz, CDCl$_3$) δ 14.42, 15.29, 15.36 (CH$_3$), 32.84 (CH$_2$), 49.98 (CH), 60.44, 61.71, 62.74 (CH$_2$O), 102.96 (CH), 116.81 (—CH$_2$), 135.05 (—CH), 172.60 (C—O).

To a cold (0°–5° C.) suspension of LiAlH$_4$ (12.25 g, 61 mmol) in 500 mL of ether was added dropwise D,L-ethyl-2-(diethoxymethyl-4-pentenoate, (13.98 g, 61 mmol) in 50 mL of ether. During the addition the temperature did not exceed 5° C. After the addition was complete, the reaction mixture was allowed to warm to room temperature. GC analysis indicated the reaction was complete (same conditions as for T$_R$ of alcohol 9.6 min). Brine was added to quench the reaction. The ether was washed with H$_2$O (1×500 mL), 2N H$_2$SO$_4$ (1×500 mL), saturated NaHCO$_3$ (1×500 mL), and brine (1×500 mL). The ether layer was dried over Na$_2$SO$_4$, and the solvent was removed under water aspirator vacuum to yield D,L-2-(hydroxymethyl)-4-pentenal-diethyl acetal, a compound having the following structure:

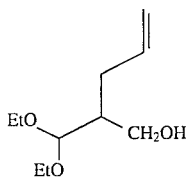

(12.89 g, quantitative yield). This was used without further purification: $^1$H—NMR (200 MHz, CDCL$_3$) δ 1.23, 1.24 (2 t, J=7.0 Hz, 6 H, CH$_3$), 1.85–2.33 (m, 3 H, HCCH$_2$C—C), 2.90 (br s, 1 H, OH), 3.45–3.89 (m, 6 H, CH$_2$O), 4.47 (d, J=5.4 Hz, 1 H, CH), 5.00–5.13 (m, 2H, H$_2$C—), 5.70–5.91 (m, 1 H, —CH); $^{13}$C—NMR (50 MHz, CDCl$_3$) δ 15.25, 15.32 (CH$_3$), 31.55 (CH$_2$), 43.19 (CH, 62.19, 62.37, 64.00 (CH$_2$O), 106.02 (CH), 116.54 (C—CH$_2$), 136.20 (—CH). Anal. Calcd for C$_{10}$H$_{20}$O$_3$: C, 63.82; H, 10.71. Found: C, 63.50; H, 10.51.

A solution containing D,L-2-(hydroxymethyl)-4-pentenal diethyl acetal (0.75 g, 4 mmol), water (8 mL), DMSO (2 mL), and CH$_3$SO$_2$OH (100 μL) was stirred for 15 h at room temperature. The reaction was monitored by GC (same as ester, t$_R$ of alcohol 9.5 min, aldehyde 5.1 min). FDP-Na$_3$ (0.560 g, 1.2 mmol) was added along with 5 mL of 20% DMSO in H$_2$O. The solution was adjusted to pH 6.8. Aldolase (350 units) and TPI (500 units) were added. The reaction was stopped after 48 h. The solution was extracted with ether (1×15 mL), and the aqueous layer was treated as before to remove the phosphate group. TLC (silica gel, ethyl acetate-methanol-H$_2$O, 12:6:2, R$_f$ of the product 0.80) indicated no fructose (R$_f$ 0.45). The solution was neutralized and freeze-dried. Trituration with ethanol, followed by removing solvent under reduced pressure, yielded a clean sample. Further purification was done (silica gel 20:4:1 ethyl acetate-methanol-water) to yield 5-allyl-5-deoxy-L-xylo-hexulose, a compound having the following structure:

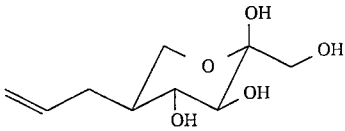

(210 mg, 1.0 mmol, 50%). Residue was crystallized from CH$_2$Cl$_2$ ether: mp 112°–3° C.; [α]$^{25}_D$ –46.5° (c 0.37, water); $^1$H—NMR (200 MHz, D$_2$O) δ 1.56 (m, 1 H, CH), 1.74 (m, 1 H, C—CCH), 2.19 (m, 1 H, C—CCH), 3.20–3.90 (m, 6 H, CHOD), 4.87 (m, 2 H, —CH$_2$), 5.66 (m, 1 H, —CH); $^{13}$C—NMR (50 MHz, D$_2$O) δ 31.68 (C5), 41.63 (C7), 62.53, 63.39, 71.80, 71.99 (CHOD), 98.11 (C2), 116.81 (—CH$_2$), 135.70 (—CH). Anal. Calcd for C$_9$H$_{16}$O$_5$: C, 52.91; H, 7.92. Found: C, 52.82; H, 7.71.

The foregoing description has been for purposes of illustration. Those skilled in the art will appreciate a number of variations and modifications therefrom. The following claims are intended to cover all modifications and variations within the true spirit and scope of the present invention.

What is claimed is:

1. A compound of the formula:

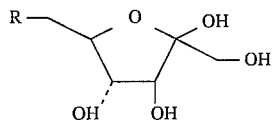

wherein R is selected from the group consisting of N$_3$, CF$_3$CONH— and C$_6$H$_5$CH$_2$OCONH—.

* * * * *